(12) United States Patent
Della Valle et al.

(10) Patent No.: US 12,370,157 B2
(45) Date of Patent: Jul. 29, 2025

(54) METHOD FOR THE TREATMENT OF COVID-19 INFECTIONS WITH PALMITOYLETHANOLAMIDE

(71) Applicants: Maria Federica Della Valle, Milan (IT); Epitech Group S.p.A., Milan (IT)

(72) Inventors: Francesco Della Valle, Milan (IT); Maria Federica Della Valle, Milan (IT); Gabriele Marcolongo, Milan (IT); Giuliano Claps, Milan (IT); Chiara Gomiero, Milan (IT); Vito Safina, Milan (IT); Annalisa Noce, Milan (IT); Salvatore Cuzzocrea, Milan (IT); Giuseppe Esposito, Milan (IT)

(73) Assignee: Epitech Group S.p.A., Milan (IT)

(*) Notice: Subject to any disclaimer, the term of this patent is extended or adjusted under 35 U.S.C. 154(b) by 765 days.

(21) Appl. No.: 17/665,894

(22) Filed: Feb. 7, 2022

(65) Prior Publication Data

US 2022/0304956 A1   Sep. 29, 2022

Related U.S. Application Data

(63) Continuation-in-part of application No. 17/213,856, filed on Mar. 26, 2021, now abandoned.

(51) Int. Cl.
| | | |
|---|---|---|
| *A61K 31/164* | (2006.01) | |
| *A61K 9/14* | (2006.01) | |
| *A61K 9/16* | (2006.01) | |
| *A61K 9/20* | (2006.01) | |
| *A61K 9/48* | (2006.01) | |
| *A61P 31/14* | (2006.01) | |

(52) U.S. Cl.
CPC ............ *A61K 31/164* (2013.01); *A61K 9/14* (2013.01); *A61K 9/1623* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/4825* (2013.01); *A61P 31/14* (2018.01)

(58) Field of Classification Search
CPC .. A61K 2300/00; A61K 31/16; A61K 31/164; A61K 9/14; A61K 9/1623; A61K 9/1688; A61K 9/2009; A61K 9/2013; A61K 9/2018; A61K 9/2027; A61K 9/2054; A61K 9/4825; A61K 9/4858; A61P 31/14; A23L 29/04; A23L 33/12; A23L 33/14

See application file for complete search history.

(56) References Cited

U.S. PATENT DOCUMENTS

2021/0338631 A1\* 11/2021 Mong ................. A61K 31/164

OTHER PUBLICATIONS

Noce (Pharmaceuticals, 2021, 14(4), 336; https://doi.org/10.3390/ph14040336). (Year: 2021).\*
Roncati et al. (Prostaglandins and Other Lipid Mediators, 154, 2021, p. 1-4) (Year: 2021).\*
Impellizzeri et al. (J of Neuroinflammation, 2014,m 11:136, pp. 1-9) (Year: 2014).\*
Accusizer (https://www.entegris.com/content/dam/product-assets/accusizers possystems/appnote-particle-size-analysis-of-active-pharmaceutical-ingredients-apis-10548.pdf, Dec. 13, 2019). (Year: 2019).\*
Gatti et al. (Pain Medicine, 2012, 13, 1121-30) (Year: 2012).\*
ClinicalTrials.gov (https://clinicaltrials.gov/ct2/show/NCT01851499, last update posted Oct. 2015). (Year: 2015).\*

\* cited by examiner

*Primary Examiner* — Umamaheswari Ramachandran
(74) *Attorney, Agent, or Firm* — MacMillan, Sobanski & Todd, LLC (57) ABSTRACT

The present invention relates to a method of treating a COVID-19 infection by administering an effective amount of an endogenous compound devoid of significant toxicity. In particular, the present invention relates to a method of treating a patient affected by COVID-19 infection comprising administering an effective amount of a mixture of ultra-micronized palmitoylethanolamide and micronized palmitoylethanolamide to said patient.

22 Claims, 8 Drawing Sheets

| Analysis | |
|---|---|
| Particle Name | PALMITOILETANOLAMIDE |
| Dispersant Name | Water |
| Dispersant Refractive Index | 1,330 |
| Scattering Model | Fraunhofer |
| Analysis Model | General Purpose |
| Laser Obscuration | 13,22 % |
| Instrument Type | Mastersizer3000 |
| Instrument Serial No. | MAL1158437 |

Figure 1

| Result | |
|---|---|
| Specific Surface Area | 3178 m²/kg |
| D [3;2] | 1,89 μm |
| D [4;3] | 2,98 μm |
| Dv (10) | 0,992 μm |
| Dv (50) | 2,55 μm |
| Dv (90) | 5,61 μm |
| Dv (100) | 12,6 μm |
| Volume Below (10) μm | 99,67 % |

Result

| Size (µm) | % Volume Under | Size (µm) | % Volume Under | Size (µm) | % Volume Under | Size (µm) | % Volume Under | Size (µm) | % Volume Under |
|---|---|---|---|---|---|---|---|---|---|
| 0,0100 | 0,00 | 0,0463 | 0,00 | 0,214 | 0,13 | 0,991 | 9,97 | 4,58 | 82,10 |
| 0,0114 | 0,00 | 0,0526 | 0,00 | 0,243 | 0,22 | 1,13 | 13,16 | 5,21 | 87,45 |
| 0,0129 | 0,00 | 0,0597 | 0,00 | 0,276 | 0,33 | 1,28 | 17,05 | 5,92 | 91,81 |
| 0,0147 | 0,00 | 0,0679 | 0,00 | 0,314 | 0,48 | 1,45 | 21,68 | 6,72 | 95,13 |
| 0,0167 | 0,00 | 0,0771 | 0,00 | 0,357 | 0,68 | 1,65 | 27,04 | 7,64 | 97,45 |
| 0,0189 | 0,00 | 0,0876 | 0,00 | 0,405 | 0,97 | 1,88 | 33,10 | 8,68 | 98,89 |
| 0,0215 | 0,00 | 0,0995 | 0,00 | 0,460 | 1,38 | 2,13 | 39,76 | 9,86 | 99,64 |
| 0,0244 | 0,00 | 0,113 | 0,00 | 0,523 | 1,96 | 2,42 | 46,88 | 11,2 | 99,94 |
| 0,0278 | 0,00 | 0,128 | 0,00 | 0,594 | 2,79 | 2,75 | 54,28 | 12,7 | 100,00 |
| 0,0315 | 0,00 | 0,146 | 0,00 | 0,675 | 3,91 | 3,12 | 61,74 | 14,5 | 100,00 |
| 0,0358 | 0,00 | 0,166 | 0,00 | 0,767 | 5,43 | 3,55 | 69,02 | 16,4 | 100,00 |
| 0,0407 | 0,00 | 0,188 | 0,06 | 0,872 | 7,42 | 4,03 | 75,88 | 18,7 | 100,00 |

Figure 1 cont.

| Size (µm) | % Volume Under | Size (µm) | % Volume Under | Size (µm) | % Volume Under | Size (µm) | % Volume Under |
|---|---|---|---|---|---|---|---|
| 21.2 | 100.00 | 98.1 | 100.00 | 454 | 100.00 | 2100 | 100.00 |
| 24.1 | 100.00 | 111 | 100.00 | 516 | 100.00 | 2390 | 100.00 |
| 27.4 | 100.00 | 127 | 100.00 | 586 | 100.00 | 2710 | 100.00 |
| 31.1 | 100.00 | 144 | 100.00 | 666 | 100.00 | 3080 | 100.00 |
| 35.3 | 100.00 | 163 | 100.00 | 756 | 100.00 | 3500 | 100.00 |
| 40.1 | 100.00 | 186 | 100.00 | 859 | 100.00 | | |
| 45.6 | 100.00 | 211 | 100.00 | 976 | 100.00 | | |
| 51.8 | 100.00 | 240 | 100.00 | 1110 | 100.00 | | |
| 58.9 | 100.00 | 272 | 100.00 | 1260 | 100.00 | | |
| 66.9 | 100.00 | 310 | 100.00 | 1430 | 100.00 | | |
| 76.0 | 100.00 | 352 | 100.00 | 1630 | 100.00 | | |
| 86.4 | 100.00 | 400 | 100.00 | 1850 | 100.00 | | |

Figure 1 cont.

| Analysis | |
|---|---|
| Particle Name | PALMITOILETANOLAMIDE |
| Dispersant Name | Water |
| Dispersant Refractive Index | 1,330 |
| Scattering Model | Fraunhofer |
| Analysis Model | General Purpose |
| Laser Obscuration | 13,32 % |
| Instrument Type | Mastersizer3000 |
| Instrument Serial No. | MAL1158437 |

Figure 2

| Result | |
|---|---|
| Specific Surface Area | 2341 m²/kg |
| D [3;2] | 2,56 µm |
| D [4;3] | 4,30 µm |
| Dv (10) | 1,31 µm |
| Dv (50) | 3,70 µm |
| Dv (90) | 8,17 µm |
| Dv (100) | 18,5 µm |
| Volume Below (10) µm | 95,61 % |

Result

| Size (μm) | % Volume Under | Size (μm) | % Volume Under | Size (μm) | % Volume Under | Size (μm) | % Volume Under | Size (μm) | % Volume Under |
|---|---|---|---|---|---|---|---|---|---|
| 0,0100 | 0,00 | 0,0463 | 0,00 | 0,214 | 0,07 | 0,991 | 5,46 | 4,58 | 61,98 |
| 0,0114 | 0,00 | 0,0526 | 0,00 | 0,243 | 0,14 | 1,13 | 7,27 | 5,21 | 69,18 |
| 0,0129 | 0,00 | 0,0597 | 0,00 | 0,276 | 0,23 | 1,28 | 9,53 | 5,92 | 76,04 |
| 0,0147 | 0,00 | 0,0679 | 0,00 | 0,314 | 0,33 | 1,45 | 12,29 | 6,72 | 82,30 |
| 0,0167 | 0,00 | 0,0771 | 0,00 | 0,357 | 0,45 | 1,65 | 15,60 | 7,64 | 87,70 |
| 0,0189 | 0,00 | 0,0876 | 0,00 | 0,405 | 0,61 | 1,88 | 19,49 | 8,68 | 92,07 |
| 0,0215 | 0,00 | 0,0995 | 0,00 | 0,460 | 0,83 | 2,13 | 23,98 | 9,86 | 95,36 |
| 0,0244 | 0,00 | 0,113 | 0,00 | 0,523 | 1,14 | 2,42 | 29,06 | 11,2 | 97,60 |
| 0,0278 | 0,00 | 0,128 | 0,00 | 0,594 | 1,56 | 2,75 | 34,73 | 12,7 | 98,96 |
| 0,0315 | 0,00 | 0,146 | 0,00 | 0,675 | 2,16 | 3,12 | 40,95 | 14,5 | 99,66 |
| 0,0358 | 0,00 | 0,166 | 0,00 | 0,767 | 2,96 | 3,55 | 47,66 | 16,4 | 99,94 |
| 0,0407 | 0,00 | 0,188 | 0,00 | 0,872 | 4,05 | 4,03 | 54,73 | 18,7 | 100,00 |

Figure 2 cont.

| Size (µm) | % Volume Under | Size (µm) | % Volume Under | Size (µm) | % Volume Under | Size (µm) | % Volume Under |
|---|---|---|---|---|---|---|---|
| 21,2 | 100,00 | 98,1 | 100,00 | 454 | 100,00 | 2100 | 100,00 |
| 24,1 | 100,00 | 111 | 100,00 | 516 | 100,00 | 2390 | 100,00 |
| 27,4 | 100,00 | 127 | 100,00 | 586 | 100,00 | 2710 | 100,00 |
| 31,1 | 100,00 | 144 | 100,00 | 666 | 100,00 | 3080 | 100,00 |
| 35,3 | 100,00 | 163 | 100,00 | 756 | 100,00 | 3500 | 100,00 |
| 40,1 | 100,00 | 185 | 100,00 | 859 | 100,00 | | |
| 45,6 | 100,00 | 211 | 100,00 | 976 | 100,00 | | |
| 51,8 | 100,00 | 240 | 100,00 | 1110 | 100,00 | | |
| 58,9 | 100,00 | 272 | 100,00 | 1260 | 100,00 | | |
| 66,9 | 100,00 | 310 | 100,00 | 1430 | 100,00 | | |
| 76,0 | 100,00 | 352 | 100,00 | 1630 | 100,00 | | |
| 86,4 | 100,00 | 400 | 100,00 | 1850 | 100,00 | | |

Figure 2 cont.

METHOD FOR THE TREATMENT OF COVID-19 INFECTIONS WITH PALMITOYLETHANOLAMIDE

FIELD OF THE INVENTION

The present invention relates to a method of treating a COVID-19 infection by administering an effective amount of an endogenous compound devoid of significant toxicity.

BACKGROUND ART

Coronaviruses (CoVs) are positive-stranded RNA viruses identified in the mid-1960s, capable of invading the epithelial cells of the respiratory and gastrointestinal tract of humans, as well as of some animals. It is also demonstrated by clinical and preclinical evidence that these viruses, particularly those belonging to the beta subtype (SARS-CoV-2 family) do not limit their presence to the respiratory tract, but can frequently invade the Central Nervous System (CNS), a capacity which is defined neurotropism, leading to the development of much more complex situations.

In a study conducted on a mouse model with a low dose of SARS-CoV-2 viral particles deposited on the nasal mucosa, it was observed that the virus invaded the CNS, the thalamus and the brainstem, even before the lung, leading to consider the possibility of a retrograde invasion of the lung starting from the brain stem, with the consequent creation of a circle capable of supporting and aggravating respiratory failure.

SARS-CoV-2 infection represents a condition characterized by a substantial systemic inflammatory storm, with a massive release of inflammatory mediators. The resulting lung damage is the result of an uncontrolled inflammatory response, characterized by excessive leukocyte infiltration and a massive release of cytokines (IL-1, IL-6, TNF and IL-8), chemokines and proteases, which promote the inflammatory process.

Because of the anomalous release of pro-inflammatory cytokines by non-neuronal cells belonging to the immune system, the organism activates a defensive neuroinflammatory process which, if not properly controlled, it can become pathological. These inflammation messengers are responsible for the destruction of the blood-brain barrier, which is followed by the aggravation of the neuroinflammatory process. In fact, following this event, the interleukins activate the Toll-like receptors located on the microglia which, in turn, recalls astrocytes, monocytes, dendritic cells, and the white blood cells that have invaded the CNS, further fueling the process, given that is confirmed by the hypertrophy of glial cells and in the death of neuronal elements. Furthermore, the breakdown of the barrier only aggravates the alterations already taking place in elderly people and even the clinically less important respiratory disorders are characterized by important inputs into the circulation of inflammatory messengers, with consequent damage to the blood-brain barrier.

The intensification of the process due to the cytokine storm justifies the fact that frequently in the patient, especially if elderly, after a viral infectious pneumonia, even if not particularly severe, the onset of a cognitive impairment syndrome may occur that lasts over time and whose treatment it is often complicated. Brain fog, cognitive deficits, memory and attention deficits, as well as delirium, are clearly caused by the cytokine storm.

SUMMARY OF THE INVENTION

The present inventors surprisingly found that the administration of a mixture of ultra-micronized palmitoylethanolamide and micronized palmitoylethanolamide to a patient affected by COVID-19 infection is able to mitigate the symptoms and to improve the prognosis of the COVID-19 infection.

Palmitoylethanolamide (PEA) is an endogenous fatty acid amide known to act through several biological mechanisms.

Micronized PEA (PEA-m) is known for example from EP 1 207 870 A1 and it is characterized by a particle size distribution mainly ranging between 2.0 and 10.0 microns as will be described thereafter.

Ultra-micronized PEA (PEA-um) is known for example from EP 2475352 A1 and it is characterized by a particle size distribution mainly ranging between 0.8 and 6.0 microns as will be described thereafter.

Preferably, the mixture PEA-um/PEA-m of the invention is used in a ratio between 3:1 and 1:1, preferably between 2.5:1 and 1.5:1, even more preferably about 2:1.

Without being bound to any theory, it is believed that the two forms of PEA described above address partly different targets. While PEA-m could almost only reach peripheral targets of the inflammatory system, PEA-um seems to be able to reach both peripheral and central targets passing the blood-brain-barrier. This was surprising, since the plasma levels of the two forms of PEA appeared to be substantially the same. This means that the ultra-micronization of PEA giving PEA-um, when compared with the conventional micronization to PEA-m, does not increase the bioavailability of the compound in a generic way, but it is able to specifically direct the drug action also to the CNS district. It can be hypothesized that the smaller particles of PEA-um, even if not solubilized, are circulating in the blood and pass through the blood-brain barrier. This is obtained with a much smaller extent with PEA-m.

DETAILED DESCRIPTION OF THE INVENTION

The present invention relates to a method of treating a patient affected by COVID-19 infection comprising administering an effective amount of a mixture of ultra-micronized palmitoylethanolamide and micronized palmitoylethanolamide to said patient.

The term "palmitoylethanolamide (or PEA) in ultra-micronized form" means PEA having a particle size distribution, defined as a percentage by volume and measured with the laser light scattering method, represented by a distribution curve having the mode below 6 microns and above 0.5 microns.

In embodiments, the PEA in ultra-micronized form (or PEA-um) has a particle size distribution as defined above, measured with a Malvern Mastersizer 3000 instrument with Fraunhofer calculation algorithm, in which at least 90% by volume of particles has a particle size of less than 6 microns.

In a preferred embodiment, PEA-um has a particle size distribution as defined above, measured with a Malvern Mastersizer 3000 instrument with Fraunhofer calculation algorithm, having a mode between 2 and 4 microns and having 100% by volume of particles smaller than 13 microns and at least 50% by volume of particles smaller than 3 microns.

The term "palmitoylethanolamide (or PEA) in micronized form" means PEA having a particle size distribution, defined as a percentage by volume and measured with the laser light scattering method, represented by a distribution curve having the mode below 8 microns and above 4 microns.

In embodiments, the PEA in micronized form (or PEA-m) has a particle size distribution as defined above, measured with a Malvern Mastersizer 3000 instrument with Fraunhofer calculation algorithm, in which at least 90% by volume of particles has a particle size of less than 9 microns.

In a preferred embodiment, PEA-m has a particle size distribution as defined above, measured with a Malvern Mastersizer 3000 instrument with Fraunhofer calculation algorithm, having a mode between 4 and 7 microns and having 100% in volume of particles smaller than 20 microns and at least 50% by volume of particles smaller than 5 microns.

The micronization can be carried out in a fluid jet plant (for example, Jetmill® model plant) which operates with "spiral technology" with a jet of compressed air or nitrogen capable of exploiting kinetic energy—instead of mechanical energy—to shatter the particles. These devices are conventional and will therefore not be further described.

However, for the preparation of PEA-um, the ultra-micronization process requires the following specific characteristics:
Internal diameter of the micronization chamber about 300 mm;
Fluid jet pressure 10-12 bar;
Product feeding 9-12 kg/hr.

In certain embodiments, the mixture PEA-um/PEA-m is used in a ratio between 3:1 and 1:1, or between 2.5:1 and 1.5:1, or about 2:1.

In certain embodiment, the amount of PEA-um per dose unit is between 200 mg and 1000 mg, or between 400 mg and 800 mg, or between 500 mg and 700 mg.

In certain embodiments, the amount of PEA-m per dose unit is between 50 mg and 800 mg, or between 150 mg and 600 mg, or between 200 mg and 400 mg.

For the purposes of the invention, the mixture PEA-um/PEA-m can be included in pharmaceutical formulations and can be formulated in dosage forms for oral, buccal, parenteral, rectal or transdermal administration.

For oral administration, the pharmaceutical compositions can be found, for example, in the form of tablets or hard or soft capsules, prepared in the conventional way with pharmaceutically acceptable excipients such as binding agents (e.g. pregelatinized maize starch, polyvinylpyrrolidone or hydroxypropyl methylcellulose); filling agents (e.g. lactose, microcrystalline cellulose or calcium hydrogen phosphate); lubricants (e.g. magnesium stearate, talc or silica); disintegrants (for example potato starch or sodium starch glycolate); or inhibiting agents (e.g. sodium lauryl sulfate). The tablets can be coated with the methods well known in the art. Liquid preparations for oral administration can be presented, for example, in the form of solutions, syrups or suspensions or can be presented as lyophilized or granulated products to be reconstituted, before use, with water or other suitable vehicles. Such liquid preparations can be prepared by conventional methods with pharmaceutically acceptable additives such as suspending agents (e.g., sorbitol syrup, cellulose derivatives or edible hydrogenated fats); emulsifying agents (e.g., lecithin or acacia); non-aqueous vehicles (e.g., almond oil, oily esters, ethyl alcohol or fractionated vegetable oils); and preservatives (e.g., methyl- or propyl-p-hydroxybenzoates or sorbic acid). The preparation may also suitably contain flavors, dyes and sweetening agents.

Preparations for oral administration can be formulated appropriately to allow controlled release of the active ingredient.

For buccal administration, the compositions may be in the form of tablets or pastilles formulated in the conventional manner, suitable for absorption at the level of the buccal mucosa. Typical buccal formulations are tablets for sublingual administration.

The composition of the invention can be formulated for parenteral administration by injection. The formulations for injections can be presented in the form of a single dose, for example in ampoules, with an added preservative. The compositions may come in this form as suspensions, solutions or emulsions in oily or aqueous vehicles and may contain formulary agents such as suspending, stabilizing and/or dispersing agents. Alternatively, the active ingredient can be found in the form of powder to be reconstituted, before use, with a suitable vehicle, for example with sterile water.

The composition of the invention can also be formulated according to rectal formulations such as suppositories or retention enema, for example containing the basic components of common suppositories such as cocoa butter or other glycerides.

In addition to the compositions described above, the composition of the invention can also be formulated as a deposit preparation. Such long-acting formulations can be administered by implantation (e.g., subcutaneously, transcutaneously or intramuscularly) or by intramuscular injection. Therefore, for example, the composition can be formulated with appropriate polymeric or hydrophobic materials (for example in the form of an emulsion in a suitable oil) or ion exchange resins or as minimally soluble derivatives.

According to the present invention, the dose of the mixture PEA-um/PEA-m proposed for administration to a man (with a body weight of about 70 kg) ranges from 200 mg to 1500 mg or from 400 mg to 1200 mg of the mixture PEA-um/PEA-m per dose unit. The dose unit can be administered, for example, 1 to 4 times a day. The dose will depend on the chosen route of administration. It should be considered that it may be necessary to make continuous changes in dosage depending on the age and weight of the patient and also on the severity of the clinical condition to be treated. The exact dose and route of administration will ultimately be at the discretion of the attending physician.

For a preventive treatment, the mixture PEA-um/PEA-m of the invention can be administered for prolonged periods or for a chronic preventive treatment, thanks to its very low toxicity.

A further object of the invention is the mixture PEA-um/PEA-m as above defined for the use in preventing and/or treating a COVID-19 infection.

Another object of the invention is the use of the mixture PEA-um/PEA-m as above defined for the manufacture of a medicament for the prevention and/or the treatment of a COVID-19 infection.

A further object of the invention are also dietary compositions, food supplements, foods for special medical purposes (FSMPs) and pharmaceutical formulations including the mixture PEA-um/PEA-m of the invention.

The term "food for special medical purposes" means products authorized according to regulation (EU) 2016/128. This term refers to a product to be administered under medical supervision, thus assimilating this FSMPs to a drug.

The formulations according to the invention can be prepared according to conventional methods, such as those described in Remington's Pharmaceutical Sciences Handbook, Mack Pub. Co., N.Y., USA, 17th edition, 1985.

Experimental Part

Micronization Process

PEA was micronized as previously described.

The ultra-micronization was carried out in a fluid jet plant (in particular, Jetmill® model plant) which operates with compressed air jet "spiral technology" modified as it follows:

internal diameter of the micronization chamber 300 mm;

fluid jet pressure 8 bar;

product feeding 9-12 kg/h.

Determination of the Particle Size Distribution

The determination of the particle size distribution was carried out on a wet sample, after 1-minute sonication.

A Malvern Mastersizer 3000 instrument operating with the LALLS technique (Low Angle Laser Light Scattering) and a Fraunhofer calculation algorithm were used.

Figure 1:
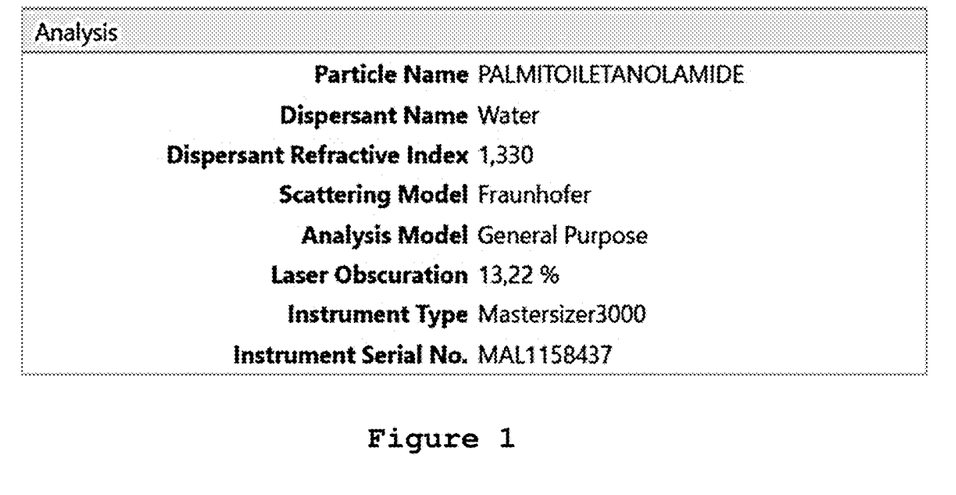
FIG. 1 shows a particle size distribution graph of palmitoylethanolamide in ultra-micronized form.
Figure 2:
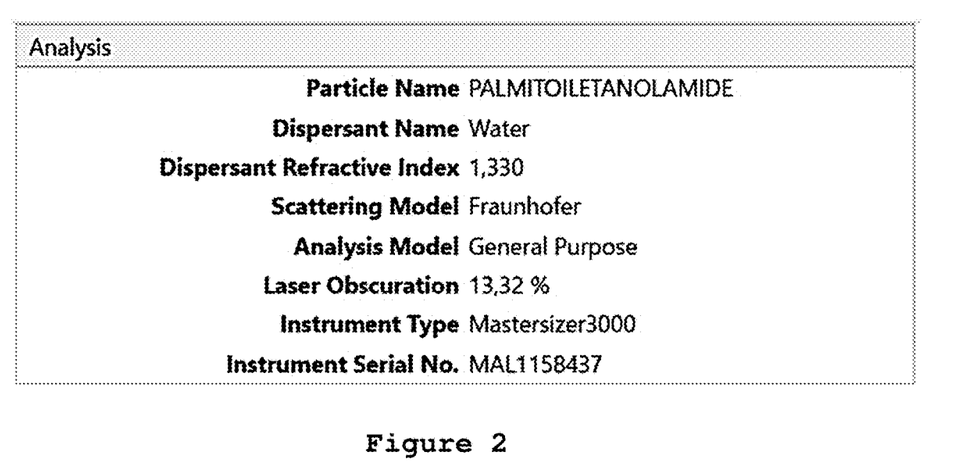
FIG. 2 shows a particle size distribution graph of palmitoylethanolamide in micronized form.

The particle size distribution graphs are shown in FIG. 1 (PEA-um) and in FIG. 2 (PEA-m).

Clinical Evidence

A 45-year-old woman, poly-allergic, tested positive for both rapid and molecular antigenic swabs, was treated orally with the mixture PEA-um/PEA-m of the invention (300 mg of PEA-m+600 mg of PEA-um) 3-times a day until the swab was negative (17 days after the onset of the symptoms). The patient suffered from headache, fatigue and physical weakness, myalgia and respiratory symptoms.

Initial chest X-ray resulted negative without showing any signs of ongoing interstitial pneumonia and blood tests showed only a mild leukocytosis with elevated total IgE (412 IU/mL) due to the known atopy. Given the absence of relevant comorbidities, the patient was discharged and immediately began therapy with the mixture PEA-um/PEA-m (tablets) in add-on to the antipyretics taken if necessary.

We surprisingly found that the administration of the mixture PEA-um/PEA-m in the first phase of the COVID-19 pathology allowed the patient to have a favorable disease course, free of manifestations such as hyperpyrexia or hyperperistalsis, loss of smell or taste and with normal oxygen saturation.

The mixture PEA-um/PEA-m of the invention represents an effective defense against COVID-19, to mitigate the symptoms and to improve the prognosis of the COVID-19 infection, with the important advantage of not weakening the cell-mediated immunity that vice versa occurs in therapies with immunosuppressants often used in this pathological context.

Clinical Study

The aim of this study is to evaluate the potential beneficial effects of administration of the PEA-um/PEA-m mixture (hereafter referred to as PEA mix) of the invention at a dose of 1800 mg/day for 28 days in a group of COVID-19 patients, compared to a group of untreated patients.

The clinical features of all enrolled patients are reported in Table 1. The two groups of the study, population A (PEA mix treated patients) and B (control group) were homogeneous for age, gender and body mass index (BMI).

TABLE 1

Clinical features of enrolled patients. The values are expressed as average ± standard deviation; $p < 0.05$ is considered statistically significant; n.s. = statistically not significant. Abbreviations: BMI, body mass index

| PARAMETERS | CASES (no. 45) | CONTROLS (no. 45) | p-value |
|---|---|---|---|
| Age (years) | 45.6 ± 13.7 | 55.8 ± 22.5 | n.s |
| Male/female (n) | 17/28 | 22/23 | n.s |
| Weight (kg) | 69.3 ± 6.9 | 70.4 ± 7.1 | n.s |
| BMI (kg/m$^2$) | 24.4 ± 3.4 | 25.6 ± 5.8 | n.s |

Inclusion criteria were: age comprised between 18-80 years, both sexes, confirmed virological COVID-19 within 24 hours with no symptoms or mild-to-moderate infection (the latter presenting one or more of the following symptoms: fever >37.5° C., cough, headache, asthenia, anosmia, diarrhea, $SpO_2$>93% or $PaO_2/FiO_2$>300 mmHg without oxygen inhalation). Exclusion criteria were: pregnancy and breast-feeding, not acceptance of the informed consent and data processing, subjects with severe respiratory failure, who require an invasive mechanic ventilation, subjects with allergy or hypersensitivity to the PEA or to one or more of its excipients.

At T0, among 90 patients, 51 were asymptomatic and 39 were mild-symptomatic. The most frequent symptoms were neurological, followed by upper respiratory tract, systemic and gastrointestinal ones. Among the neurological manifestations, most patients presented anosmia, ageusia, muscular aches and headache. The upper respiratory tract manifestations were represented by dry caught, dyspnea and sore throat. Systemic symptoms were represented by fever >37.5° C. and by asthenia. Gastrointestinal symptoms were rare and consisted of diarrhea and nausea.

Treatment

All enrolled patients were in home-based isolation and they were randomized into two groups, according to the study protocol: the first group (45 patients) received oral treatment in microgranules for sublingual use containing the mixture PEA-um/PEA-m of the invention and the second group (45 patients) represented the control group. The first group assumed 2 sticks of PEA mix (one stick contains 600 mg PEA-um and 300 mg PEA-m) per day (morning and evening) at dose of 1800 mg/day for 28 days.

Patients in both groups received standard treatments: Non-Steroidal Anti-Inflammatory drugs (NSAIDs) such as Nimesulide 100 mg/day and paracetamol (1000 mg every 8 hours) in case of fever >38° C.

At T0 and T1, all enrolled patients underwent to the following laboratory exams: complete blood count, erythrocyte sedimentation rate (ESR), biomarkers of liver and renal function, muscle damage indices, vitamin D, complete blood clotting test (D-dimer test), CRP, IL-6, TNF-α, and lymphocyte subpopulations. Moreover, the following inflammatory indices were calculated: platelets-to-lymphocytes, neutrophils-to-lymphocytes and lymphocytes-to-monocytes ratios. At T1, COVID-19 serological response was also evaluated.

Complete blood count was determined by automated method (Dasit-Sysmex, Milan, Italy), ESR with the fully automated analyzer test-1 (Alifax Srl, Polverara, Padova, Italy), CRP was analyzed by the immunoturbidimetric method (Abbott Diagnostics, Milan, Italy). Routine laboratory parameters were evaluated by Abbott Architect Instrument (Abbott Diagnostics Milan, Italy).

Muscle damage indices (Creatine kinase-CPK and myoglobin) were evaluated using a chemiluminescence immunoassays with Abbott Architect Instrument (Abbott Diagnostics, Milan, Italy).

Total serum vitamin D was measured by electrochemiluminescence (Abbott Architect Instrument, Milan, Italy). Blood clotting test was detected by ACLTOP (Werfen, Milan, Italy). Serum levels of IL-6 were measured by chemiluminescence (IMMULITE 2000, Siemens, Milan, Italy), on the other hand, TNF-α levels were measured by ELISA technique (DRG, International Instruments GmbH, Marburg, Germany).

Lymphocyte subpopulations (CD3+ and CD8+ absolute count) were assessed by flow cytometric analysis, performed on whole blood samples, obtained from venous sampling. Samples were incubated with anti-CD3 and anti-CD8 fluorescent monoclonal antibodies (mAbs) and using FACSCanto II with two lasers and up to 6-7 colours (BD, Biosciences) and FACSDiva Software (BD, Biosciences) for acquisition and analysis. The samples were first incubated with mAbs and then processed with the red cell lysing (using 1× ammonium chloride solution; BD, Bioscience). Moreover, all patients also underwent to capillary sampling, using CR4000 tool for the evaluation of oxidative stress (OS) and for the assessment of antioxidant defense mechanisms. In particular, a FORT and a FORD tests were performed. The first test detects the levels of circulating oxygen free radicals and the second test indirectly determines blood antioxidant defenses. Anti-SARS-CoV2 IgG levels were determined with Elecsys Anti-SARS-CoV2 S immunoassay (Roche Diagnostics International Ltd. Rotkreuz, CH.

All parameters were analyzed according to standard procedures in the Clinical Chemical Laboratories of the University Hospital, PTV of Rome.

Table 2 reports relevant data proving the activity of the PEA mix of the invention.

ecules like DNA, lipids, and proteins. In fact, they are able to induce a high production of reactive oxygen species (ROS), triggering and amplifying a dysregulated immune response. Moreover, these viruses can cause an upregulated nitric oxide synthase-2 (NOS2) expression. In view of the obtained results, PEA mix may be useful in counteracting OS and inflammation, as it seems to be able to decrease the ROS production and, at the same time, to modulate positively the release of pro-inflammatory cytokines, mitigating the clinical symptoms.

Furthermore, in PEA mix-treated group, it is noted an increased trend of FORD (data not shown), namely the antioxidant defenses. During SARS-CoV-2 infection, the amplified ROS production induces a consequent reduction of human antioxidant defenses with an increased susceptibility to severe pictures of disease, especially in elderly patient and in those affected by chronic-degenerative non-communicable diseases. Therefore, the antioxidant properties of PEA mix could attenuate the COVID-19 complications and the tissue damage in several organs and systems.

It has also been found a significant reduction of neutrophil-to-lymphocytes ratio in the PEA mix-treated group. This index is a negative prognostic parameter in patients with sepsis and it is an indicator of systemic inflammation. The neutrophil-to-lymphocytes ratio, easily available, has been recently proposed and it has been recognized as an independent predictor for several pathological conditions like cancer, cardiovascular diseases etc. In particular, the increase of this index has been associated with higher mortality in hospitalized COVID-19 patients. The normal values of neutrophil-to-lymphocytes ratio, in healthy adult subjects, are comprised between 1.0 and 2.3. In detail, the study showed a normalization of this ratio only in the PEA mix-treated group.

In the treated-group of patients, it is also noted a significant increase of CD3+ and CD8+ lymphocyte subpopulation

TABLE 2

Main results observed in case and control groups. $p < 0.05$ is considered statistically significant.
Abbreviations: CRP: C-reactive Protein; FORT: Free Oxygen Radicals Test; IL, interleukin; NA, not available

| PARAMETERS | CASES (NO. 45) | | CONTROLS (NO. 45) | | p-value |
|---|---|---|---|---|---|
| | T0 (mean ± SD) | T1 (mean ± SD) | T0 (mean ± SD) | T1 (mean ± SD) | |
| Neutrophil-to-Lymphocyte ratio | 2.43 ± 2.03 | 1.78 ± 3.8 | 3.45 ± 4.64 | 2.7 ± 3.16 | 0.04 |
| D-Dimer (ng/mL) | 686.19 ± 1348.77 | 366.07 ± 230.76 | 1032 ± 1258.42 | 670.57 ± 507.08 | 0.0001 |
| CRP (mg/dL) | 7.20 ± 12.95 | 1.55 ± 1.80 | 20.03 ± 24.59 | 9.79 ± 16.90 | 0.007 |
| IL-6 (pg/mL) | 11.22 ± 19.58 | 3.30 ± 1.54 | 24.20 ± 23.00 | 15.36 ± 19.90 | 0.0001 |
| FORT (U) | 271.07 ± 156.82 | 222.02 ± 107.71 | 229.90 ± 143.98 | 283.30 ± 111.08 | 0.05 |
| CD3+ CD8+ absolute count | 526.98 ± 330.71 | 636.41 ± 325.26 | 497.13 ± 237.31 | 487.60 ± 196.81 | 0.0001 |
| Anti- SARS-Cov-2 IgG (U/ml) | NA | 4.37 ± 1.62 | NA | 2.89 ± 2.03 | 0.0001 |

The significant reduction of inflammatory status observed in the PEA mix-treated patients seems to contrast the onset of neuroinflammation and the OS. In fact, the study shows a significant decrease of CRP and IL-6 after 28 days of PEA mix assumption in the treated group. We also observed a trend of TNF-α reduction in the same group (data not reported), even if it is not statistically significant.

Another important result is the significant increase of OS in the control group at T1 and on the contrary a reduction in the PEA mix treated group, as derivable from the FORT test. It is well-known that several interstitial viruses, including SARS-CoV-2, cause an enhancement of oxidized biomolecules at T1. This elevation may be correlated to the PEA mix treatment, as the mixture seems to prevent the "consumption" of T-cells and the worsening of the COVID-19 versus more severe clinical manifestations. In accordance with previous studies, these data confirm that PEA mix is able to directly modulate T-cells response by the regulation of inflammatory pathways.

Another parameter related to a poor survival in COVID-19 patients is represented by D-dimer levels. The enhancement of this biomarker, indicative of activation of coagulation pathways and thrombosis, has been associated with unfortunate prognosis in the early stages of COVID-19 patients. Interestingly, in this study the oral assumption of PEA mix seems to counteract this increase, that is commonly found in COVID-19 clinical evolution, suggesting that the mixture could display a protective effect against vascular damage. In fact, normal values of D-dimer, in healthy adult subjects, are comprised between 0 and 500 ng/ml. Thus, the study showed a normalization of this value only in the PEA mix-treated group.

Finally, it is observed a prompt and better response of immune system in the treated group compared to the control one, tested by total antibodies against SARS-CoV-2. In fact, in treated patients a higher antibody title compared to the controls was observed. The presence of antibodies against SARS-CoV-2 may be the best indicator of protection against the reinfection.

In view of the above data, other objects of the invention are:
i) a method of increasing anti-SARS-CoV-2 IgG levels in a subject, comprising or consisting of the administration to such a subject of a mixture of ultra-micronized palmitoylethanolamide and micronized palmitoylethanolamide as defined in present specification;
ii) the method of point i), wherein the administration of the mixture of ultra-micronized palmitoylethanolamide and micronized palmitoylethanolamide also induces a normalization of the D-dimer level and/or the neutrophil-to-lymphocyte ratio;
iii) the method of point i) and/or ii), wherein the administration of the mixture of ultra-micronized palmitoylethanolamide and micronized palmitoylethanolamide also induces a decrease of more than 50% of the IL-6 levels and/or a decrease of more than 60% of the CRP levels;
iv) the method of any one of points i) to iii), wherein the administration of the mixture of ultra-micronized palmitoylethanolamide and micronized palmitoylethanolamide also induces an increase of the CD3+ and CD8+ plasma levels and a decrease of the free radical oxygen species in the plasma;
v) the method of any one of points i) to iv), wherein the subject is an asymptomatic or mild-symptomatic COVID-19 patient.

EXAMPLES OF FORMULATIONS

Example 1

Each tablet contains:
PEA-um mg 600
PEA-m mg 300
Microcrystalline cellulose 122 mg
Croscarmellose sodium 135 mg
Polyvinylpyrrolidone 45 mg
Magnesium stearate 11 mg
Colloidal silica mg 6
35 mg coating.

Example 2

Each tablet contains:
PEA-um 400 mg
PEA-m mg 200
Microcrystalline cellulose 157 mg
Croscarmellose sodium 90 mg
Polyvinylpyrrolidone 20 mg
Magnesium stearate 8 mg
Polysorbate 80 mg 4.

Example 3

Each hard gelatin capsule contains:
PEA-um mg 200
PEA-m mg 200
Lactose 100 mg

Example 4

A 5 g dose of gold-dispersible microgranules contains:
PEA-um mg 600
PEA-m mg 600
Non-cariogenic sugar 300 mg
Pharmacologically acceptable excipients q.b. to 5 g.

Example 5

Each soft gelatin capsule contains:
PEA-um mg 100
PEA-m mg 200
Oily excipients 300 mg.

What we claim is:

1. A method of treating a patient affected by COVID-19 infection comprising administering an effective amount of a mixture of ultra-micronized palmitoylethanolamide and micronized palmitoylethanolamide to said patient, wherein the mixture of ultra-micronized palmitoylethanolamide and micronized palmitoylethanolamide is administered in a ratio between 3:1 and 1:1.

2. The method of claim 1, wherein the ultra-micronized palmitoylethanolamide has a particle size distribution, defined as a percentage by volume and measured with the laser light scattering method, represented by a distribution curve having the mode below 6 microns and above 0.5 microns.

3. The method of claim 2, wherein the ultra-micronized palmitoylethanolamide has a particle size distribution, measured with a Malvern Mastersizer 3000 instrument with Fraunhofer calculation algorithm, in which at least 90% by volume of particles has a particle size of less than 6 microns.

4. The method of claim 2, wherein the ultra-micronized palmitoylethanolamide has a particle size distribution, measured with a Malvern Mastersizer 3000 instrument with Fraunhofer calculation algorithm, having a mode between 2 and 4 microns and having 100% by volume of particles smaller than 13 microns and at least 50% by volume of particles smaller than 3 microns.

5. The method of claim 1, wherein the micronized palmitoylethanolamide has a particle size distribution, defined as a percentage by volume and measured with the laser light scattering method, represented by a distribution curve having the mode below 8 microns and above 4 microns.

6. The method of claim 5, wherein the micronized palmitoylethanolamide has a particle size distribution, measured with a Malvern Mastersizer 3000 instrument with Fraunhofer calculation algorithm, in which at least 90% by volume of particles has a particle size of less than 9 microns.

7. The method of claim 5, wherein the micronized palmitoylethanolamide has a particle size distribution, measured with a Malvern Mastersizer 3000 instrument with Fraunhofer calculation algorithm, having a mode between 4 and 7 microns and having 100% in volume of particles smaller than 20 microns and at least 50% by volume of particles smaller than 5 microns.

8. The method of claim 1, wherein the mixture of ultra-micronized palmitoylethanolamide and micronized palmitoylethanolamide is administered in a ratio between 2.5:1 and 1.5:1.

9. The method of claim 8, wherein the mixture of ultra-micronized palmitoylethanolamide and micronized palmitoylethanolamide is administered in a ratio of about 2:1.

10. The method of claim 1, wherein the mixture of ultra-micronized palmitoylethanolamide and micronized palmitoylethanolamide is included in a pharmaceutical formulation and it is formulated in dosage forms for oral, buccal, parenteral, rectal or transdermal administration.

11. The method of claim 10, wherein the amount of ultra-micronized palmitoylethanolamide per dose unit is between 200 mg and 1000 mg.

12. The method of claim 11, wherein the amount of ultra-micronized palmitoylethanolamide per dose unit is between 400 mg and 800 mg.

13. The method of claim 10, wherein the amount of micronized palmitoylethanolamide per dose unit is between 50 mg and 800 mg.

14. The method of claim 13, wherein the amount of micronized palmitoylethanolamide per dose unit is between 150 mg and 600 mg.

15. The method of claim 10, wherein the dosage form is administered one to four times a day.

16. The method of claim 1, wherein the mixture of ultra-micronized palmitoylethanolamide and micronized palmitoylethanolamide is included in dietary compositions, food supplements and foods for special medical purposes (FSMPs).

17. The method of claim 1, wherein the mixture of ultra-micronized palmitoylethanolamide and micronized palmitoylethanolamide is administered for prolonged periods.

18. A method of increasing anti-SARS-COV-2 IgG levels in a subject, comprising the administration to such a subject of a mixture of ultra-micronized palmitoylethanolamide and micronized palmitoylethanolamide, wherein the mixture of ultra-micronized palmitoylethanolamide and micronized palmitoylethanolamide is administered in a ratio between 3:1 and 1:1.

19. The method of claim 18, wherein the administration of the mixture of ultra-micronized palmitoylethanolamide and micronized palmitoylethanolamide also induces a normalization of the D-dimer level and/or the neutrophil-to-lymphocyte ratio.

20. The method of claim 18, wherein the administration of the mixture of ultra-micronized palmitoylethanolamide and micronized palmitoylethanolamide also induces a decrease of more than 50% of the IL-6 levels and/or a decrease of more than 60% of the CRP levels.

21. The method of claim 18, wherein the administration of the mixture of ultra-micronized palmitoylethanolamide and micronized palmitoylethanolamide also induces an increase of the CD3+ and CD8+ plasma levels and a decrease of the free radical oxygen species in the plasma.

22. The method of claim 18, wherein the subject is an asymptomatic or mild-symptomatic COVID-19 patient.

\* \* \* \* \*